United States Patent [19]
Burkinshaw

[11] Patent Number: 6,045,581
[45] Date of Patent: Apr. 4, 2000

[54] IMPLANTABLE PROSTHESIS HAVING TEXTURED BEARING SURFACES

[75] Inventor: Brian D. Burkinshaw, Pflugerville, Tex.

[73] Assignee: Sulzer Orthopedics Inc., Austin, Tex.

[21] Appl. No.: 08/989,751

[22] Filed: Dec. 12, 1997

[51] Int. Cl.$^7$ .................................................. A61F 2/30
[52] U.S. Cl. ................................................. 623/18; 623/20
[58] Field of Search .................................. 623/18, 22, 23, 623/20, 19; 403/29, 53

[56] References Cited

U.S. PATENT DOCUMENTS

| | | | |
|---|---|---|---|
| 3,512,184 | 5/1970 | Grove | 623/18 |
| 4,865,603 | 9/1989 | Noiles | 623/18 |
| 5,152,794 | 10/1992 | Davidson | 623/20 |
| 5,645,601 | 7/1997 | Pope et al. | 623/23 |
| 5,662,158 | 9/1997 | Caldarise | 164/456 |
| 5,683,468 | 11/1997 | Pappas | 623/20 |
| 5,782,927 | 7/1998 | Klawitter et al. | 623/21 |

FOREIGN PATENT DOCUMENTS

128220  1/1984  European Pat. Off. .................. 623/16

OTHER PUBLICATIONS

Foster, L., GEO–METRICSII, pp. 34–37, 68–72, 76–77.
Informational Brochure, REGMI–TECH,LTD.
Moore, W.R., Foundations of Mechanical Accuracy, 1970, pp. 20–30, B–2–B8,1–6,33–35, 65–69, 124–133.

*Primary Examiner*—Bruce E. Snow
*Attorney, Agent, or Firm*—Philip S. Lyren; Kenneth S. Barrow

[57] ABSTRACT

An implantable orthopedic prosthesis includes a first component having a first bearing surface, and a second component having a second bearing surface. The second bearing surface is disposed in opposition to the first bearing surface in a sliding bearing relationship. At lease one of the first and second bearing surfaces includes a plurality of substantially evenly distributed plateaus interspersed with valleys. The plateaus comprise at least about 30% of the gross area of the bearing surface. The plateaus are distributed at a density of about 18 to about 25 plateaus per square inch of gross area of the bearing surface. The first and second bearing surfaces are substantially congruent to each other, and the plateaus have a smooth surface finish of less than about 8 $\mu$m root mean square. The valleys have a depth of about 0.0002 inch to about 0.002 inch below the plateaus to facilitate lubrication of the articulating surfaces by natural body fluids.

10 Claims, 6 Drawing Sheets

IMPLANTABLE PROSTHESIS HAVING TEXTURED BEARING SURFACES

BACKGROUND OF THE INVENTION

Field of the Invention

The present invention relates generally to implantable prostheses for replacing human skeletal joints, and relates more particularly to the surface characteristics of prosthetic articulation surfaces of such implantable prostheses.

BACKGROUND INFORMATION

Implantable orthopedic prostheses, in one form, comprise manufactured replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip joint and the knee joint are most often treated with such prostheses. The hip and knee joints are major weight bearing joints and degenerate more quickly than other joints in case of abnormality. Also, the hip and knee joints play a critical role in ambulation and quality of life, resulting in great demand for surgical correction of abnormalities.

The human hip joint involves two bones: the femur and the pelvis, each having a smooth articulation surface arranged for articulation against an adjacent articulation surface of the other bone. The femur includes at its proximal extremity a head having a convex, generally spherically contoured articulation surface. The pelvis, in pertinent part, includes an acetabulum having a concave, generally spherically contoured articulation surface. The mutually engaging articulation surfaces of the femur and the pelvis together form, functionally, a ball-and-socket joint.

One or both of the articulation surfaces of the hip joint may fail to act properly, requiring the defective natural articulation surface to be replaced with a prosthetic articulation surface provided by an implantable prosthesis. To fit defects of varying scope, while allowing healthy portions of the hip joint to be conserved, a range of types of orthopedic implants is available. The range extends from total hip prosthesis systems for replacing the articulation surfaces of both the femur and the pelvis, to less comprehensive systems for replacing only the femoral articulation surface. Commonly employed orthopedic hip prostheses include components that fall within one of three principle categories: femoral stems, femoral heads and acetabular cups. A so-called "total" hip prosthesis includes components from each of these categories. The femoral stem replaces the proximal end of the femur and includes a distal stem received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled to suit the anatomical needs of the patient. A so-called "bipolar" hip prosthesis includes only femoral stem and head components. The femoral part of the hip joint is replaced with a femoral stem supporting an artificial femoral head. The latter includes an inner head, fixed to the femoral stem, that articulates within an outer head. The outer head articulates directly against the natural acetabulum. Similarly, a so-called "unipolar" hip prosthesis also includes only femoral stem and head components. The femoral part of the hip joint is replaced with a femoral stem supporting an artificial femoral head. The femoral head articulates directly against the natural acetabulum while remaining fixed relative to the femoral stem.

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anterior-posterior direction. The condyles join at the distal-anterior face of the femur to form a patellar surface having a shallow vertical groove as an extension of the intercondylar groove. The patella includes on its posterior face an articulation surface having a vertical ridge separating medial and lateral convex facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patellofemoral joint, and the mutually engaging articulation surfaces of the femur and tibia together form, functionally, the tibiofemoral joint, which two functional joints together form the anatomical knee joint.

One or more of the articulation surfaces of the knee joint may fail to act properly, requiring the defective natural articulation surface to be replaced with a prosthetic articulation surface provided by an implantable prosthesis. To fit defects of varying scope, while allowing healthy portions of the knee joint to be conserved, a range of types of orthopedic knee implants is available. The range extends from total knee prosthesis systems for replacing the entire articulation surface of each of the femur, tibia and patella, to simpler systems for replacing only the tibiofemoral joint, or only one side (medial or lateral) of the tibiofemoral joint, or only the patellofemoral joint. Commonly employed orthopedic knee prostheses include components that fall within one of three principle categories: femoral components, tibial components, and patellar components. A so-called "total" knee prosthesis includes components from each of these categories. The femoral component replaces the distal end and condylar articulating surfaces of the femur and may include a proximal stem received within the medullary canal at the distal end of the femur. The tibial component replaces the proximal end and meniscal articulating surfaces of the tibia and may include a distal stem received within the medullary canal at the proximal end of the tibia. The patellar component replaces the posterior side and natural articulating surface of the patella. Sometimes, the patellar component is not used, and the natural articulating surface of the patella is allowed to articulate against the femoral component. A so-called "unicondylar" knee prosthesis replaces only the medial or the lateral femoral condylar articulating surface and the corresponding tibial meniscal articulating surface.

The acetabular cup component of a total hip prosthesis is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball-and-socket joint to restore motion to a defective hip joint.

One known type of acetabular cup involves an acetabular shell made of a biocompatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. As used herein, the words proximal and distal are terms of reference that indicate a particular portion of a prosthesis component according to the relative disposition of the portion when the component is implanted. "Proximal" indicates that portion of a component nearest the torso, whereas "distal" indicates that portion of the component farthest from the torso. Between the dome and rim, the acetabular shell comprises a shell wall defined by a generally convex proximal surface and a generally concave distal surface spaced from the proximal surface. The concave distal surface defines a shell cavity having an opening at the rim of the cup for receiving the bearing insert. The bearing insert has a generally convex proximal surface configured to be received and fixed within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component. The acetabular shell can be affixed to the acetabular bone by bone screws or bone cement. If bone screws are elected, the screws are driven into the bone through the screw holes before the bearing insert is placed into the shell. The shell also can be affixed by a combination of bone screws and bone cement.

Other known types of acetabular cup vary from the type described above, among other ways, by including a bearing insert, or more particularly, an articulating surface of a bearing insert, made of a material other than polyethylene. Such other materials include metals and metal alloys, such as cobalt chrome, and ceramics.

The tibial component of a total knee prosthesis is configured to be received upon and fixed to the proximal end of the tibia. The tibia is prepared to receive the tibial component by resecting part of the proximal end of the tibia to leave a substantially horizontal planar bony plateau. Sometimes the exposed medullary canal at the proximal end of the tibia is also reamed to receive a stem portion of the tibial component. The tibial component typically includes a plate portion having an inferior planar surface conforming to the resected bony plateau at the proximal end of the femur. The plate portion may or may not include a depending stem or keel for receipt within a prepared tibial medullary canal. Commonly, a meniscal bearing insert is received atop the plate portion of the tibial component to provide an artificial meniscal articulating surface for receiving the condylar surfaces of the femoral component of the total hip prosthesis. The femoral condylar articulating surfaces articulate against the tibial meniscal articulating surface to restore motion to a defective knee joint.

One known type of tibial component involves a tibial plate made of a biocompatible metal such as titanium or a titanium alloy, and a meniscal bearing insert made of a bio-compatible polymer such as ultra-high molecular weight polyethylene. The tibial plate is shaped generally as a flat plate having a perimeter that generally conforms to the transverse sectional perimeter of the resected proximal tibia. The tibial plate includes a planar distal, or inferior, surface for engaging the resected proximal tibia, and a proximal, or superior, surface for engaging and receiving the meniscal bearing insert. One or more screw holes may extend through the plate portion from the superior to the inferior surface. The bearing insert has an inferior surface that engages the superior surface of the plate portion, and may include locking tabs or other means for fixing the bearing insert to the plate portion against relative movement. The tibial plate can be affixed to the resected tibial bone by bone screws or bone cement. If bone screws are elected, the screws are driven into the bone through the screw holes before the bearing insert is placed atop the plate portion. The plate also can be affixed by a combination of bone screws and bone cement. The tibial bearing insert usually is designed to be received atop the tibial plate in nonarticulating relative relationship. In some total knee prostheses, however, the bearing insert is intended to articulate on the tibial plate in sliding or rotating relationship. Such knee prostheses are known as "mobile bearing" knees.

According to a prevailing hypothesis, sliding motion between adjacent metal and polyethylene surfaces in implanted joint prostheses generates fine polyethylene particulate debris due to frictional wear. The generation of such debris is hypothesized to occur even at metal-to-polyethylene interfaces that are not designed to articulate. This is believed to occur from unintended relative micromotion between the metal and polyethylene surfaces caused by the varying load borne by the implanted prosthesis in use. In reaction to this hypothesis, some manufacturers of implantable joint prostheses have begun to polish the metal surfaces in their products that are in non-articulating engagement with polyethylene components, just as they previously polished the metal surfaces that were known and intended to articulate against polyethylene. The reason for concern over such polyethylene wear debris is that in vitro experiments have shown that fine polyethylene particles are osteolytic. Whether this osteolytic action occurs in vivo is not known. Nevertheless, given the concern over the issue of wear debris being generated at non-articulating interfaces, it would be desirable to avoid sliding interfaces between metal surfaces and polyethylene surfaces in implantable joint prostheses, at least in those applications where the frictional characteristics of a metal-to-polyethylene interface is not required for proper operation of the artificial joint.

In the case of the mobile bearing type knee prothesis, it has been proposed to bond the polyethylene meniscal bearing insert to a metal substrate which slides against the metal tibial plate. This results in a polished metal-to-polyethylene interface between the femoral component and the meniscal bearing insert, in combination with a metal-to-metal sliding interface between the meniscal bearing insert and the tibial plate. One problem associated with such a metal-to-metal sliding interface is the need to prevent metal wear debris from being generated. Conventionally, the solution to this problem is to make each of the metal sliding surfaces highly polished, as has been done in some types of prosthetic hip joints. Highly polished metal femoral heads articulating against highly polished concave spherical acetabular bearing surfaces have been used successfully for many years, particularly in Europe.

The polished metal-to-metal articulating interface, as used in some prosthetic hip joints, is known to provide a prosthesis having excellent wear resistance. Nevertheless, the sliding friction between such polished metal surfaces is also known to be greater than the sliding friction between polyethylene and polished metal. The greater friction of the polished metal-to-metal interface results in a tendency toward greater resistance to rotation of the joint. This phenomenon has been restrained within reasonable limits in the case of ball and socket hip joints by limiting the diameter of the spherical metal head. That solution is not readily applicable to the planar metal-to-metal interface of a mobile bearing knee prosthesis, as the area of the interface is dictated by the range of sliding motion to be achieved and cannot be limited arbitrarily. This problem can be alleviated somewhat by substituting other hard materials having lower coefficients of friction. For example, one surface of the interface could be made of a polished ceramic material, while the other surface is made of a polished metal. Alternatively, both surfaces could be made of polished ceramic. This approach is not believed to fully address the problem, as the resulting sliding friction would still be significantly greater than that of a metal-to-polyethylene interface.

It would be desirable to provide a sliding interface in an implantable joint prosthesis that preserves the desirable wear resistance characteristics of a metal-to-metal, metal-to-ceramic, or ceramic-to-ceramic interface, while significantly reducing the sliding friction of such interfaces. This and other desirable advantages are achieved by the present invention.

SUMMARY OF THE INVENTION

According to one aspect of the present invention, an implantable orthopedic prosthesis includes a first component having a first bearing surface, and a second component having a second bearing surface. The second bearing surface is disposed in opposition to the first bearing surface in a sliding bearing relationship. At least one of the first and second bearing surfaces includes a plurality of substantially evenly distributed plateaus interspersed with valleys. The plateaus comprise at least about 30% of the gross area of the bearing surface.

According to other aspects of the present invention, the plateaus are distributed at a density of about 18 to about 25 plateaus per square inch of gross area of the bearing surface. The plateaus have a smooth surface finish of less than about 8 $\mu$m root mean square, and the valleys have a depth of about 0.0002 inch to about 0.002 inch below the plateaus.

It is an object of the present invention to provide an implantable orthopedic prosthesis having a sliding interface between components having good wear characteristics and low frictional resistance to sliding.

Other objects and advantages of the present invention will be apparent from the following descriptions of the preferred embodiments illustrated in the drawings.

BRIEF DESCRIPTION OF THE DRAWINGS

FIG. 1b is an enlarged sectional view of the surface of FIG. 1a.

FIG. 7a is a bottom plan view of a mobile, meniscal bearing insert according to the present invention for use with the tibial baseplate component of FIG. 6a.

FIG. 8 is an assembly sectional view of the tibial baseplate of FIG. 6a and the mobile, meniscal bearing insert of FIG. 7a.

FIG. 10b is a cross-sectional view of the tibial component of FIG. 10a.

FIG. 11b is a cross-sectional view of the tibial component of FIG. 11a.

FIG. 12b is a cross-sectional view of the tibial component of FIG. 11a.

DESCRIPTION OF THE PREFERRED EMBODIMENTS

The present invention is concerned with the surface texture characteristics of opposed bearing surfaces of components of an implantable orthopedic prosthesis arranged in a sliding bearing relationship. In general, the surfaces of the preferred embodiments provide polished bearing regions dispersed substantially evenly over the gross surface area. The polished regions comprise plateaus disposed within a narrow-tolerance surface profile that is flat, cylindrical, conical or spherical. Between the plateau regions are valley regions of sufficient depth to hold and provide pathways for the natural lubricating body fluids in the skeletal joint. By way of introduction, the features and characteristics of such surfaces according to the present invention are described below with respect to FIGS. 1a–5. Following the introductory explanation, the preferred embodiments of such surfaces are described in the context of exemplary hip and knee prosthetic components, with reference to FIGS. 6a–13.

Figure 1A:
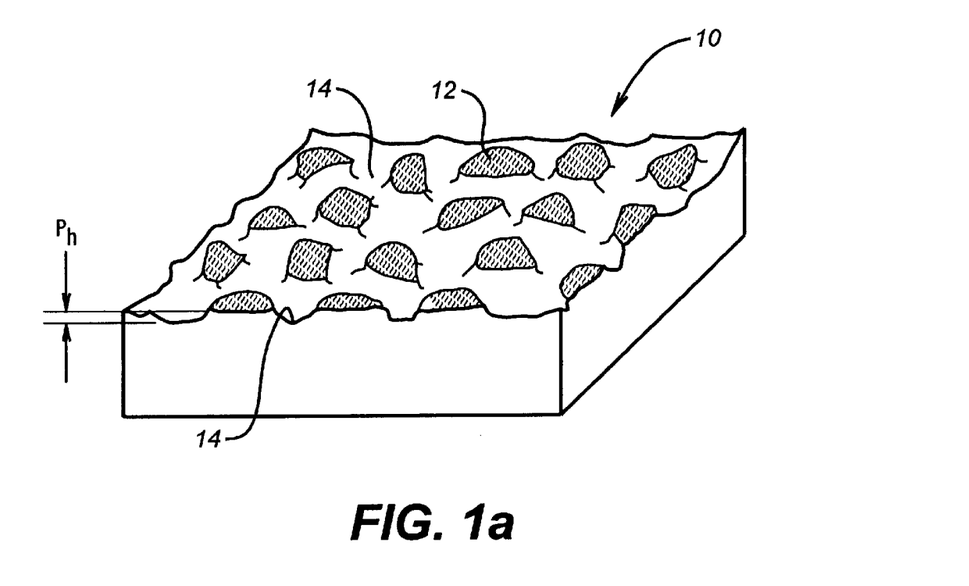
FIG. 1a is a perspective sectional view of an arbitrary portion of a surface according to the present invention.
Figure 1B:
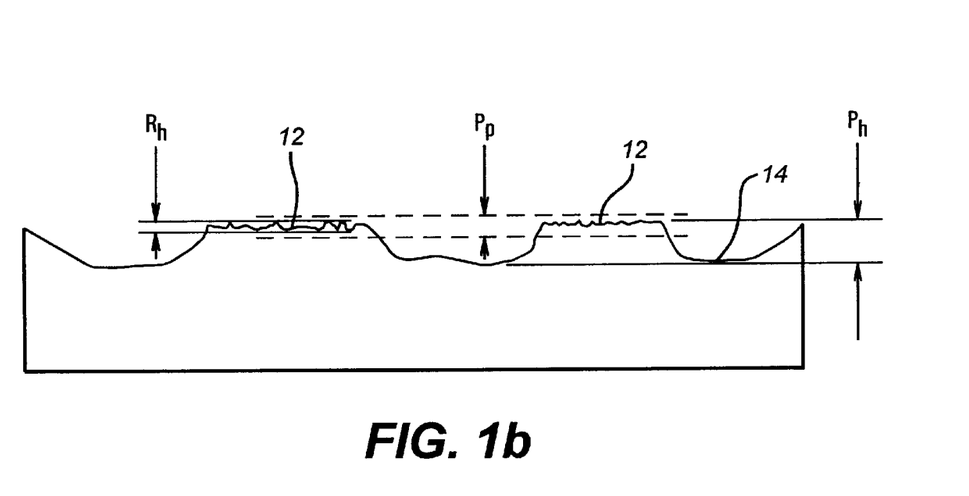

Referring to FIGS. 1a and 1b, an arbitrary section of a surface 10 is shown. Surface 10 can be described with respect to the following characteristics, as annotated in FIGS. 1a and 1b with the following respective reference symbols: Roughness height, $R_h$; plateau height, $P_h$; and plateau profile, $P_p$. From a macroscopic perspective, surface 10 is considered as having high areas, or plateaus, 12, and low areas, or valleys, 14, interspersed between the plateaus 12. The height differential between the plateaus and the valleys is the plateau height, $P_h$. From an even larger macroscopic perspective, surface 10 is considered as having a plateau profile, $P_p$, which represents the high and low limits between which a region of surface 10 must lie to be regarded as a plateau 10. All regions lying below the lower limit of the plateau profile $P_p$ are regarded as valley areas 14. From a microscopic perspective, the plateau regions 12 of surface 10 are considered as having a roughness height, $R_h$, which represents the high and low limits between which adjacent microscopic peaks and troughs of surface 10 must lie for the respective plateau region to be regarded as having a specified surface finish. Qualitatively, the plateau height specification $P_h$ has the broadest limits, the plateau profile specification $P_p$ has narrower limits, and the surface roughness specification of the plateaus 12, $R_h$, has the narrowest limits.

Figure 2:
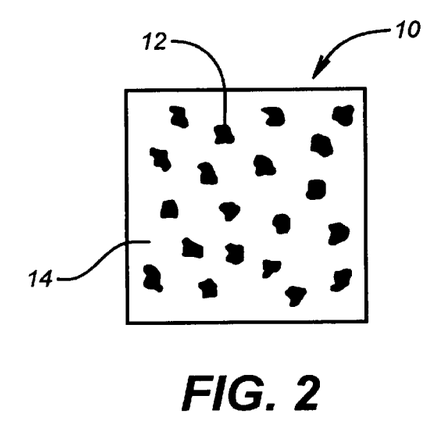
FIGS. 2–5 are plan views of arbitrary portions of surfaces according to the present invention, useful for understanding surface parameters.
Figure 3:
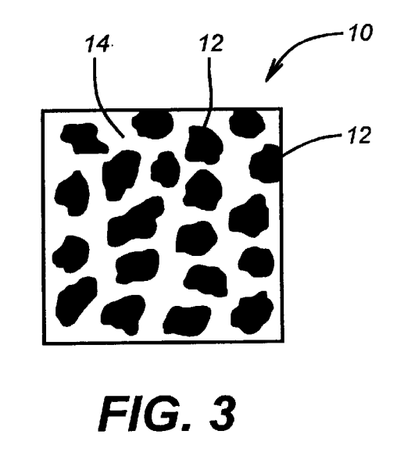
Figure 4:
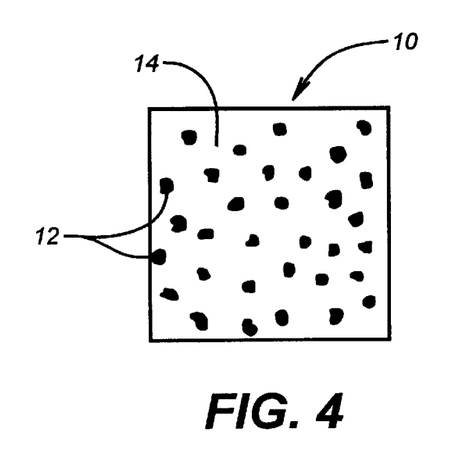
Figure 5:
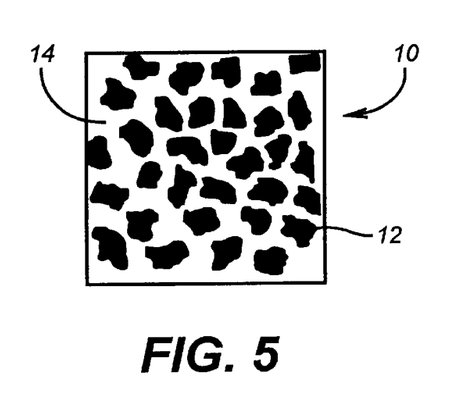

Referring to FIGS. 2–5, plan views of alternative configurations of surface 10 are illustrated, showing regions of about one square inch. FIGS. 2–5 illustrate differing percentages of the gross surface area of surface 10 occupied by plateau regions 12. All gross surface area not regarded as a plateau area 12 is regarded as valley area 14. In FIGS. 2 and 4, the plateaus 12 occupy 10% of the gross surface area of surface 10. In FIGS. 3 and 5, the plateaus 12 occupy 40% of the gross surface area of surface 10. FIGS. 2–5 also illustrate differing numbers of plateaus 12 per square inch of gross surface area of surface 10. In FIGS. 2 and 3, there are twenty plateaus 12 per square inch of gross surface area. In FIGS. 4 and 5, there are thirty-two plateaus 12 per square inch of gross surface area. By comparing all four figures, FIGS. 2–5, the effect of altering the relative area occupied by the plateaus 12 and of altering the absolute number of plateaus 12 per unit area can be appreciated.

It is a purpose of the present invention to provide mutually opposed, mating, sliding bearing surfaces of an implantable orthopedic prosthesis with surface features that reduce the sliding friction between the two surfaces, that enhance lubrication of the sliding bearing surfaces by natural body fluids, and that maintain a high resistance to wear. This purpose is accomplished by fabricating the sliding bearing surfaces according to these principles: (1) each surface is held within close tolerances with respect to plateau profile, $P_p$, the plateau profile being flat, cylindrical, conical, spherical, or other contour as dictated by the required performance of the prosthesis; (2) the roughness height, $R_h$, of the surface within each plateau region is held within close tolerances of about 8 μm root mean square; (3) the percentage of gross surface area occupied by the plateau regions is at least about 30%; (4) the distribution density of the plateau regions is held between about 18 and about 25 plateau regions per square inch of gross surface area; and (5) the distribution pattern of the plateau regions can be regular or random, and can be provided on one or both of the opposed bearing surfaces, provided that the distribution is such that no mutually interlocking arrangement is possible between the patterns of the two surfaces. The plateau height, Ph, is preferred to be between about 0.0002 inch and about 0.002 inch. The material of the bearing surfaces, as preferred, is a bio-compatible metal such as titanium, titanium alloy, or cobalt chrome alloy, or a ceramic material, or a suitably hard, biocompatible coating, e.g., DLC, over a biocompatible substrate.

According to the present invention, the surface 10 is fabricated by the following method steps. First, a metal component, on which surface 10 is to be generated, is shaped by conventional casting, forging or milling techniques to the desired configuration of the component. The surface which is to become surface 10 is then milled or ground to conform to the desired plateau profile, Pp. In other words, if the surface profile is desired to be flat, for example, the metal surface is made flat within the profile tolerance band, Pp. Alternatively, the profile could be cylindrical, conical, spherical or another shape, as required by the design goals for the component. Second, the valley regions 14 are formed by hand scraping, machine tooling, or other appropriate metal forming technique to conform to the desired depth specified by the plateau height, Ph. Incidental to this step is the formation of the plateau regions 12 which constitute that portion of the surface generated in the first step that is not disturbed by the operation of the second step. The total area, distribution, and density of the plateau regions 12 is maintained within the desirable ranges discussed above by controlling the valley forming operation. Third, the plateau regions resulting from the second step are ground or lapped, to remove any burrs or other protrusions that may have resulted from the second step, to restore the plateau profile, Pp, within specifications. Fourth, the plateau regions are polished to conform to the roughness height, Rh, specifications.

Referring to FIGS. 6a–8, a first preferred embodiment of an orthopedic joint prostheses is shown and described in general terms, and with regard to specific bearing surfaces incorporating the surface characteristics discussed above. Surface features and parameters that correspond to the general terms discussed above with regard to FIGS. 1a–5 are indicated by like primed reference symbols.

Figure 6A:
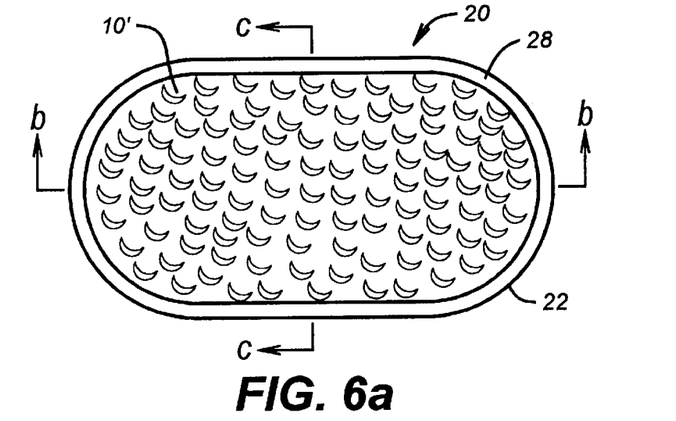
FIG. 6a is a top plan view of a tibial baseplate component according to the present invention.
Figure 6B:
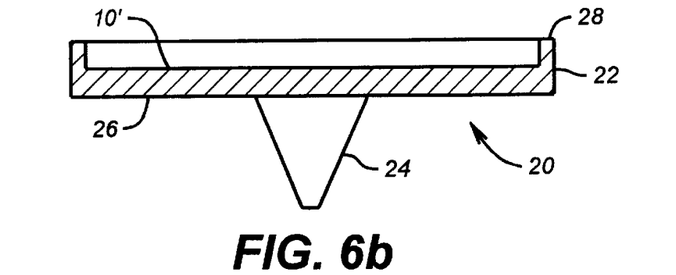
FIG. 6b is a sectional view of the tibial baseplate of FIG. 6a, taken in the plane b—b of FIG. 6a and viewed in the direction of the arrows.
Figure 6C:
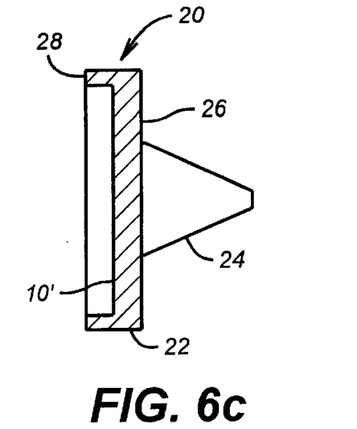
FIG. 6c is a sectional view of the tibial baseplate of FIG. 6a, taken in the plane c—c of FIG. 6a and viewed in the direction of the arrows.

With particular reference to FIGS. 6a–6c, a tibial component 20 of a total knee prosthesis is shown. Tibial component 20 includes a tibial plate 22 and a distal keel 24 extending distally from plate 22 for receipt within the medullary canal at a resected proximal end of a tibia. Plate 22 includes a distal surface 26 for engagement with and affixation to the resected bony plateau at the proximal end of the tibia. Plate 22 also includes a proximal sliding bearing surface 10' bounded by an upstanding peripheral wall 28.

Figure 7A:
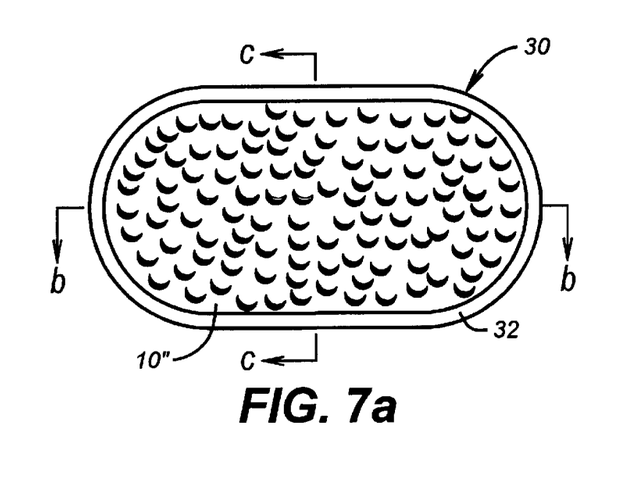
Figure 7B:
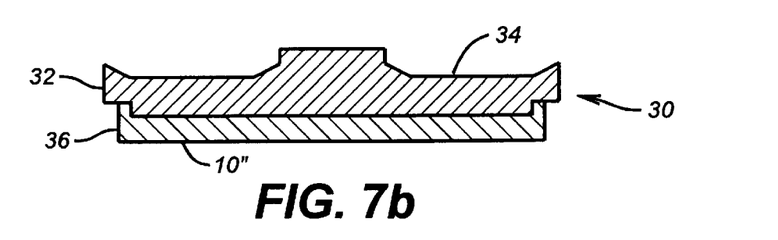
FIG. 7b is a sectional view of the mobile, meniscal bearing insert of FIG. 7a, taken in the plane b—b of FIG. 7a and viewed in the direction of the arrows.
Figure 7C:
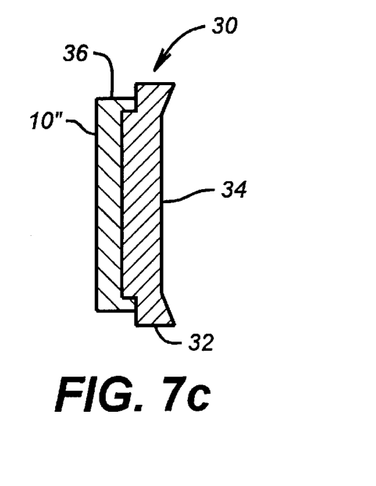
FIG. 7c is a sectional view of the mobile, meniscal bearing insert of FIG. 7a, taken in the plane c—c of FIG. 7a and viewed in the direction of the arrows.

Referring now to FIGS. 7a–7c, a mobile, meniscal bearing insert 30 of a total knee prosthesis, for use with the tibial component 20 of FIGS. 6a–6c, is shown. Bearing insert 30 includes a meniscal bearing 32 having a proximal articulation surface 34 for articulating against distal femoral condyle articulation surfaces 42 of a femoral component 40, shown in FIG. 9, of a total knee prosthesis. Affixed to the distal side of meniscal bearing 32 is a mobile bearing plate 36 having a distal sliding bearing surface 10".

Figure 8:
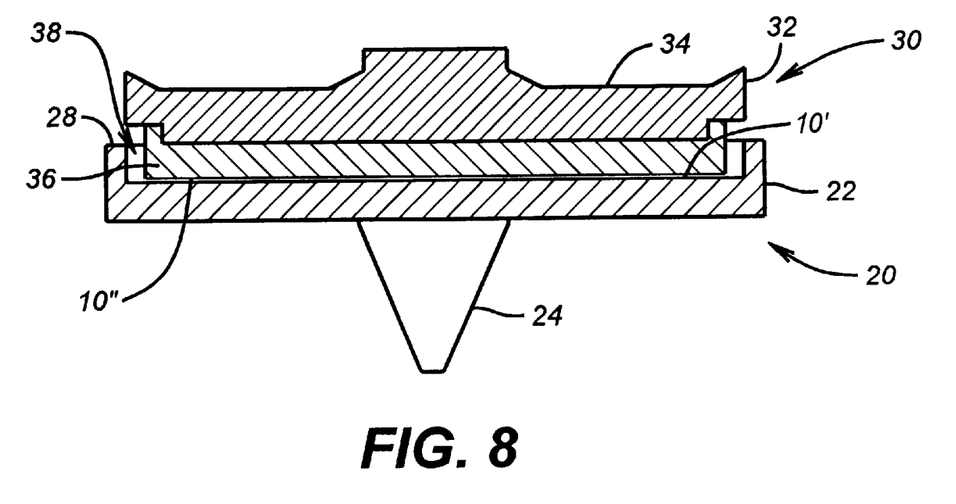
Figure 9:
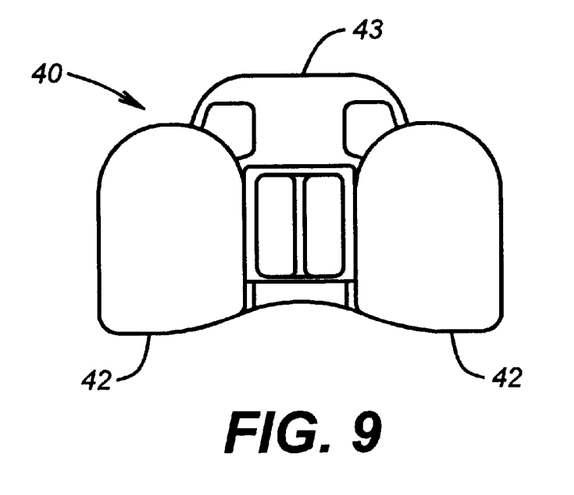
FIG. 9 is an elevation view of a femoral component according to the present invention.

In FIG. 8, the tibial component 20 of FIGS. 6a–6c is shown assembled to the mobile, meniscal bearing insert 30 of FIGS. 7a–7c. Proximal sliding bearing surface 10' is disposed in opposition to and in sliding engagement with distal sliding bearing surface 10". Because the medial-lateral and anterior-posterior dimensions of mobile bearing plate 36 are less than the corresponding dimensions of the interior surface of upstanding wall 28, a perimetrical gap 38 exists between wall 28 and plate 36, permitting sliding translation of meniscal bearing insert 30 relative to tibial component 20. This characteristic is referred to by the term "mobile" in the phrase mobile bearing knee prosthesis.

As preferred, surfaces 10' and 10" of tibial plate 22 and mobile bearing plate 36, respectively, are made of a biocompatible metal such as titanium, titanium alloy, or cobalt chrome alloy. Alternatively, one or both of surfaces 10' and 10" could be made of a ceramic material, or of a suitably hard, biocompatible coating, e.g., DLC, over a biocompatible substrate. Surface 34 of mensical bearing 32, as preferred, is made of ultra-high molecular weight polyethylene. Other materials, such as metal or ceramic, can be substituted for surface 34 according to the performance characteristics desired for the articulating interface between the meniscal bearing insert 32 and the femoral component 40, shown in FIG. 9. As another alternative, only one of surfaces 10' and 10" need be generated according to the present invention. The other opposed sliding bearing surface could have a plateau profile, Pp, that is substantially zero. In other words, one of the opposed bearing surfaces could be textured according to the present invention while the other is uniformly polished over its entire gross surface area.

Figure 10A:
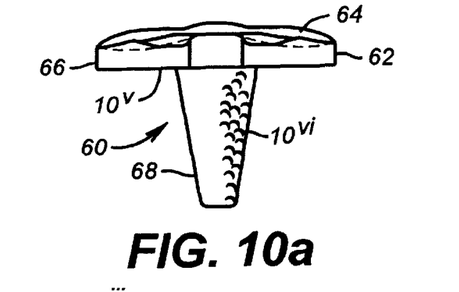
FIG. 10a is an elevational view of a mobile, meniscal bearing insert according to a second embodiment of the the present invention.
Figure 10B:
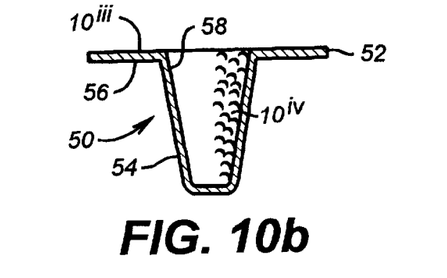
Figure 11A:
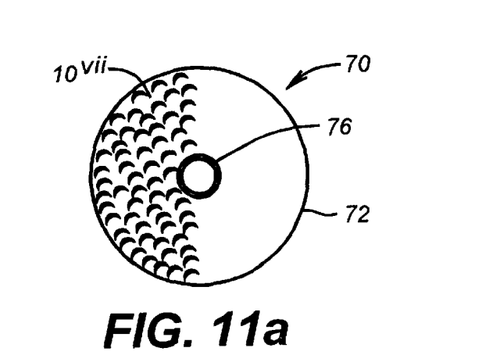
FIG. 11a is an anterior view of a patellar bearing insert according to a third embodiment of the present invention.
Figure 11B:
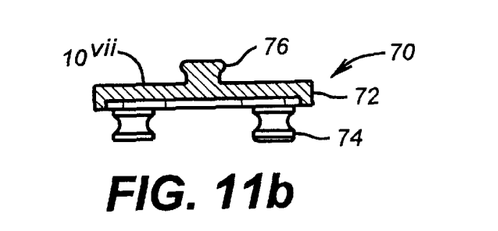
Figure 12A:
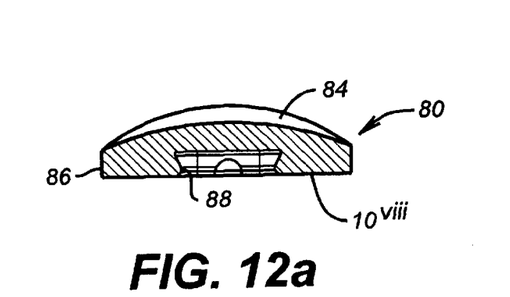
FIG. 12a is a cross-sectional view of a patellar bearing insert according to a third embodiment of the present invention.
Figure 12B:
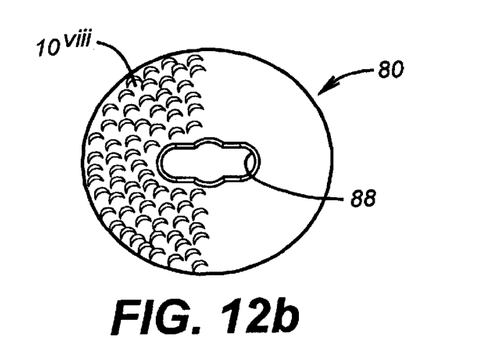

Referring now to FIGS. 10a and 10b, a second embodiment of the present invention is illustrated, comprising a tibial component 50 and a mobile, meniscal bearing insert 60, also known as a rotating platform. As in the description of the first embodiment of FIGS. 6–8, above, surface features and parameters that correspond to the general terms discussed above with regard to FIGS. 1a–5 are indicated by like primed reference symbols. Likewise, the preferred materials of which the bearing surfaces can be constructed are the same as those described with respect to that first embodiment. Tibial component 50 includes a tibial plate 52 and a distal keel 54 extending distally from plate 52 for receipt within the medullary canal at a resected proximal end of a tibia. Plate 52 includes a distal surface 56 for engagement with and affixation to the resected bony plateau at the proximal end of the tibia. Plate 52 also includes a proximal sliding bearing surface $10'''$. Keel 54 is hollow and opens proximally through plate 52. An inner wall 58 of hollow keel 54 is shaped as a truncated cone. Conical inner wall 58 has a conical sliding bearing surface $10^{iv}$. Bearing insert 60 includes a meniscal bearing 62 having a proximal articulation surface 64 for articulating against the distal femoral condyle articulation surfaces 42 of the femoral component 40, shown in FIG. 9. Affixed to the distal side of meniscal bearing 62 is a mobile bearing plate 66 having a distal sliding bearing surface $10^{v}$. Depending from mobile bearing plate 66 is a frusto-conical stem 68 having an outer conical sliding bearing surface $10^{vi}$. As implanted, stem 68 of bearing insert 60 is received within the hollow of keel 54 of tibial component 50, such that bearing surface $10^{vi}$ is received in rotary sliding engagement with bearing surface $10^{iv}$, while bearing surface $10^{v}$ is disposed in sliding engagement with bearing surface $10'''$.

Referring now to FIGS. 11a–12b, a third embodiment of the present invention is illustrated, comprising a patellar base component 70 and a mobile patellar bearing insert 80. As in the description of the embodiments of FIGS. 6–8 and 10a and 10b, above, surface features and parameters that correspond to the general terms discussed above with regard to FIGS. 1a–5 are indicated by like primed reference symbols. Likewise, the preferred materials of which the bearing surfaces can be constructed are the same as those described with respect to the first embodiment of FIGS. 6–8. Patellar component 70 includes a base plate 72 and anterior pegs 74 extending anteriorly from plate 72 for receipt within corresponding holes drilled in a resected posterior surface of the patella. Plate 72 also includes a posterior sliding bearing surface $10^{vii}$ and a peg 76 extending posteriorly therefrom. Patellar bearing insert 80 includes a posterior articulation surface 84 for articulating against the anterior patellar articulation surface 43 of the femoral component 40, shown in FIG. 9. Affixed to the anterior side of patellar bearing insert 80 is a mobile bearing plate 86 having a distal sliding bearing surface $10^{viii}$. Recessed through mobile bearing plate 86 is an undercut elongate slot 88 in which peg 76 is received in a snap-fit relationship. As implanted, bearing surface $10^{viii}$ is disposed in sliding engagement upon bearing surface $10^{vii}$.

Figure 13:
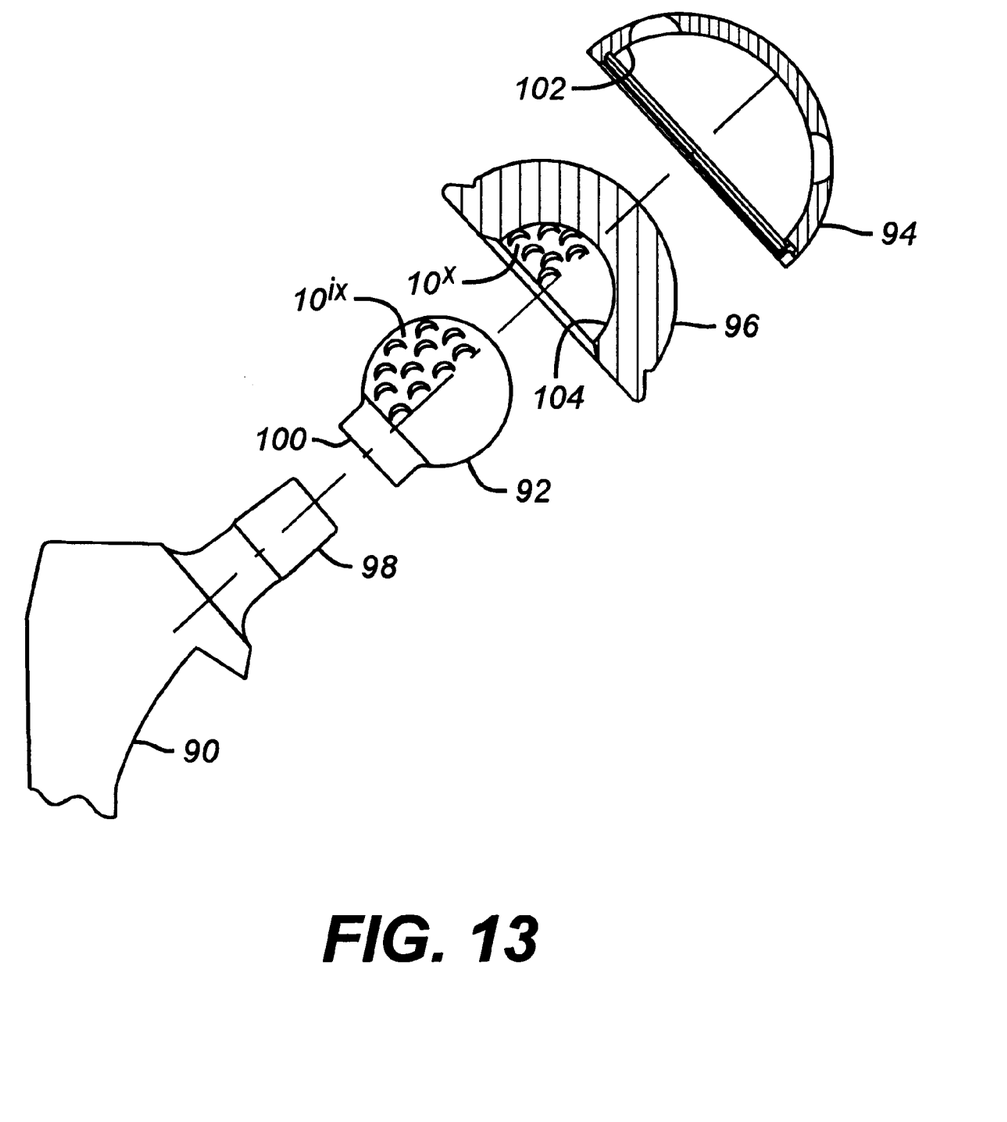
FIG. 13 is an exploded view, partially in section of an implantable orthopedic hip prosthesis according to the present invention.

Referring now to FIG. 13, a further embodiment of the present invention is illustrated, comprising a femoral hip stem component 90, a femoral head component 92, and an acetabular cup comprising a shell 94 and a bearing insert 96. As in the description of the other embodiments described above, surface features and parameters that correspond to the general terms discussed above with regard to FIGS. 1a–5 are indicated by like primed reference symbols. Likewise, the preferred materials of which the bearing surfaces can be constructed are the same as those described with respect to the first embodiment of FIGS. 6–8. Stem component 90 includes a male conical taper neck 98 for receipt within a female conical bore 100 within head 92. Shell component 94, shaped generally as a hemispherical cup, includes a cavity 102 in which bearing insert 96 is received in fixed engagement. Insert 96, preferably made of a ceramic material, includes a cavity 104 in which head 92 is received in articulating relationship. The spherical surface of head 92 includes a bearing surface $10^{ix}$. Likewise, the spherical inner surface of cavity 104 of bearing insert 96 includes a bearing surface $10^{x}$. As implanted, bearing surface $10^{ix}$ engages and articulates against bearing surface $10^{x}$.

The present invention has been illustrated and described with particularity in terms of preferred embodiments. Nevertheless, it should be understood that no limitation of the scope of the invention is intended. The scope of the invention is defined by the claims appended hereto. It should also be understood that variations of the particular embodiments described herein incorporating the principles of the present invention will occur to those of ordinary skill in the art and yet be within the scope of the appended claims.

I claim:

1. An implantable orthopedic prosthesis comprising:
   a first component having a first bearing surface;
   a second component having a second bearing surface, said second bearing surface being disposed in opposition to said first bearing surface in a sliding bearing relationship;
   at least one of said first and second bearing surfaces including a plurality of substantially evenly distributed plateaus interspersed with valleys;
   said plateaus being distributed at a density of about 18 to about 25 plateaus per square inch; and
   said plateaus having a smooth surface finish of less than about 8 µm root mean square.

2. The implantable orthopedic prosthesis of claim 1, in which said first and second bearing surfaces are substantially congruent to each other.

3. The implantable orthopedic prosthesis of claim 1, in which said valleys have a depth of about 0.0002 inch to about 0.002 inch below said plateaus.

4. The implantable orthopedic prosthesis of claim 1 in which said plateaus are distributed on said first bearing surface and comprise at least 30% of the area of said first bearing surface.

5. The implantable orthopedic prosthesis of claim 1 in which said plateaus are distributed on both said first bearing surface and said second bearing surface and comprise at least 30% of the area of said first and second bearing surfaces.

6. An implantable orthopedic prosthesis comprising:
   a tibial component having a proximal bearing surface;
   a tibial mobile, meniscal bearing insert having a distal bearing surface, said distal bearing surface being disposed in opposition to said proximal bearing surface of said tibial component in a sliding bearing relationship;
   at least one of said proximal and distal bearing surfaces including a plurality of substantially evenly distributed plateaus interspersed with valleys;
   said plateaus being distributed at a density of about 18 to about 25 plateaus per square inch of gross area of the bearing surface; and said plateaus having a smooth surface finish of less than about 8 µm root mean square.

7. The implantable orthopedic prosthesis of claim 6, in which said first and second bearing surfaces are substantially congruent to each other.

8. The implantable orthopedic prosthesis of claim 6, in which said valleys have a depth of about 0.0002 inch to about 0.002 inch below said plateaus.

9. The implantable orthopedic prosthesis of claim 6 in which said plateaus are distributed on said first bearing surface and comprise at least 30% of the area of said first bearing surface.

10. The implantable orthopedic prosthesis of claim 6 in which said plateaus are distributed on both said first bearing surface and said second bearing surface and comprise at least 30% of the area of said first and second bearing surfaces.

* * * * *